(12) United States Patent
Eckles et al.

(10) Patent No.: US 10,863,769 B2
(45) Date of Patent: Dec. 15, 2020

(54) MOUTHPIECE FOR SMOKING AND VAPORIZING DEVICES

(71) Applicant: NATIONAL CONCESSIONS GROUP INC., Denver, CO (US)

(72) Inventors: Mike Eckles, San Juan, PR (US); Chris McElvany, Denver, CO (US); Andrew Rexroad, Denver, CO (US)

(73) Assignee: National Concessions Group Inc., Denver, CO (US)

( * ) Notice: Subject to any disclaimer, the term of this patent is extended or adjusted under 35 U.S.C. 154(b) by 185 days.

(21) Appl. No.: 15/938,910

(22) Filed: Mar. 28, 2018

(65) Prior Publication Data

US 2018/0279670 A1    Oct. 4, 2018

Related U.S. Application Data

(60) Provisional application No. 62/477,853, filed on Mar. 28, 2017.

(51) Int. Cl.
*A24F 7/02*    (2006.01)
*A61M 15/00*    (2006.01)
*A24F 47/00*    (2020.01)

(52) U.S. Cl.
CPC .............. *A24F 7/02* (2013.01); *A24F 47/008* (2013.01); *A61M 15/0021* (2014.02)

(58) Field of Classification Search
CPC ........................................................ A24F 2/007
USPC ........................................................ 131/329
See application file for complete search history.

(56) References Cited

U.S. PATENT DOCUMENTS

| | | | |
|---|---|---|---|
| 2009/0151717 A1* | 6/2009 | Bowen ................. | A61M 11/048 128/200.23 |
| 2014/0196735 A1* | 7/2014 | Liu ........................ | A24F 47/008 131/329 |
| 2014/0283857 A1* | 9/2014 | Liu ........................ | A24F 47/008 131/329 |
| 2015/0128969 A1* | 5/2015 | Chapman .............. | A24F 47/008 131/329 |
| 2016/0021933 A1* | 1/2016 | Thorens ................ | A24F 47/008 131/329 |
| 2017/0238617 A1* | 8/2017 | Scatterday ............ | A24F 47/008 |

* cited by examiner

*Primary Examiner* — Eric Yaary
(74) *Attorney, Agent, or Firm* — Sheridan Ross P.C.

(57) ABSTRACT

A mouthpiece device is provided for interconnection with a personal vaporizer device. The mouthpiece is connectable to a cartridge and comprises connection members to securely interconnect the mouthpiece and the cartridge. In some embodiments, at least one connection member is provided that is detachable from a remainder of the mouthpiece to prevent tampering with a mouthpiece or a cartridge.

20 Claims, 8 Drawing Sheets

MOUTHPIECE FOR SMOKING AND VAPORIZING DEVICES

This U.S. Non-Provisional Patent Application claims the benefit of priority from U.S. Provisional Patent Application Ser. No. 62/477,853, filed Mar. 28, 2017, the entire disclosure of which is hereby incorporated by reference.

FIELD

The present disclosure relates generally to systems, devices and methods for vaporizing and smoking accessories. More specifically, the present disclosure and various embodiments disclosed herein relate to mouthpieces for connecting to a cartridge or other component of a smoking or vaporizing accessory. Such accessories include but are not limited to pen-style vaporizing devices.

BACKGROUND

Conventional smoking methods and devices are characterized by igniting a substance, and inhaling smoke resulting from the combustion of that substance. Smoking can cause serious health issues, including respiratory system diseases and cancer. Despite known risks, however, smoking remains a popular method for intaking chemicals and other substances, such as nicotine, various herbs and tetrahydrocannabinol (TEC), to name a few.

In recent years, the electronic cigarette or "e-cigarette" has seen increased use and acceptance as an alternative to traditional smoking methods. E-cigarettes and related devices include the provision of a liquid or oil and a heating element vaporizes the oil and the resulting vapor is inhaled. In some of these devices, the oil is provided in a replaceable cartridge. When the cartridge is empty, it is removed and replaced with a full cartridge. The oil cartridge will include a connector that mates with a complementary connector associated with the c-cigarette or pen.

Cartridges are typically provided with an interconnected mouthpiece. The mouthpiece provides a user-interface for the device, which is typically sized to conform to and contact a user's mouth at least during the act of smoking or inhaling. Applicant has determined that conventional attachment means, devices and methods for securing mouthpieces to cartridges pose various issues and risks. Specifically, Applicant has discovered that existing mouthpiece devices are subject to various risks including, but not limited to, intentional tampering with the mouthpiece or cartridge, and unintended damage to the cartridge and/or mouthpiece from normal handling. Applicant has also determined that existing mouthpieces, cartridges, and associated connecting devices and features result in a labor and time-intensive assembly process.

SUMMARY

It is therefore an object of the present disclosure to provide an improved mouthpiece assembly that improves upon prior art devices and addresses various problems associated therewith. Specifically, it is an object of the present disclosure to provide a mouthpiece with an improved connection for receiving or otherwise attaching to a cartridge.

In various embodiments, an improved connection is provided for a mouthpiece and wherein the mouthpiece attaches to a cartridge in a secure yet easy-to-assemble manner. In certain embodiments, a mouthpiece is provided that comprises at least one flexible attachment member that is operable to contact a cartridge. Preferably, the at least one connecting member comprises a flexible member with a frangible score line that is operable to be severed and detach the at least one connecting member from the cartridge upon breakage or excessive manipulation of the mouthpiece. The detachment of the at least one connecting member from the cartridge results in the member being deposited in a portion of the cartridge. The cartridge is thereafter rendered inoperable and inaccessible such that it cannot be reused or refilled.

In various embodiments, the present disclosure provides mouthpieces that comprise at least one and preferably a plurality of connecting members that extend from portions of the mouthpiece and are operable to connect to and secure a cartridge. Connecting members are contemplated as comprising flexible members having at least some plasticity wherein the members are operable to be deformed upon engagement with the cartridge, and wherein the members are operable to expand or otherwise regain an original shape or position after a step of assembling the mouthpiece and the cartridge is completed. Connecting members of the present disclosure provide for an improved assembly process at least with respect to a mouthpiece and a cartridge, and wherein the mouthpiece may be securely connected to the cartridge by simple press-fitting of the two components.

In one embodiment, a mouthpiece for a personal vaporizer device is provided that comprises a first end operable to contact the mouth of a user, a second end operable to connect to a cartridge, the second end comprising an open end and a recessed portion provided within a partially enclosed interior volume. At least one connecting member extends from the recessed portion, and the at least one connecting member is operable to receive and connect to a cartridge. At least one connecting member comprises a flexible member and a frangible score line and wherein the at least one connecting member comprises a severable feature.

The Summary of the Invention is neither intended nor should it be construed as being representative of the full extent and scope of the present disclosure. The present disclosure is set forth in various levels of detail in the Summary as well as in the attached drawings and the Detailed Description and no limitation as to the scope of the present disclosure is intended by either the inclusion or non-inclusion of elements, components, etc. in this Summary. Additional aspects of the present disclosure will become more readily apparent from the Detailed Description, particularly when taken together with the drawings.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosure.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

Figure 1:
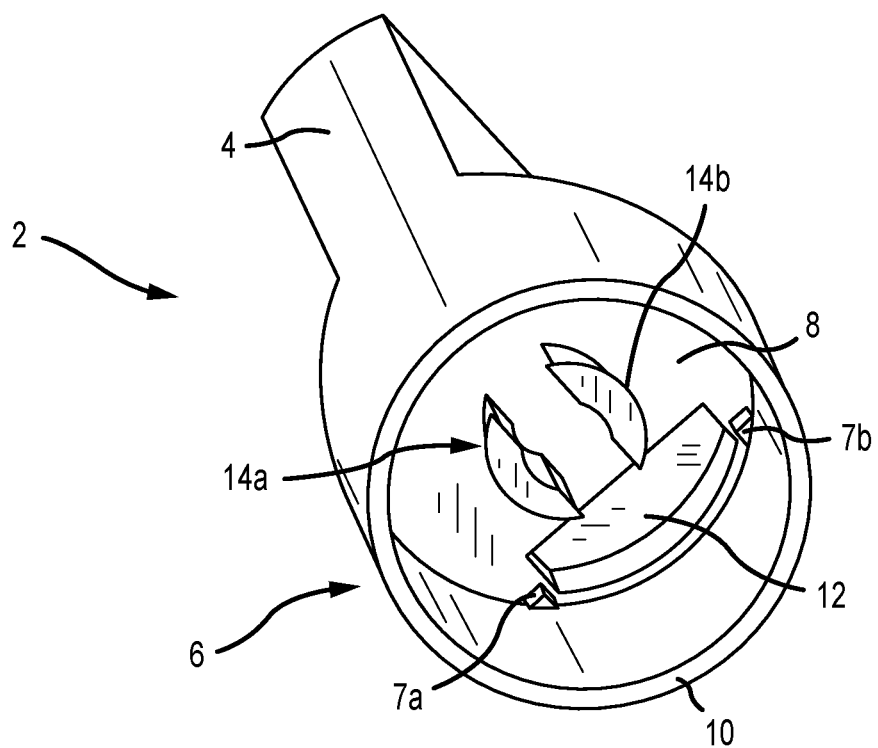

FIG. 1 is a perspective view of a mouthpiece according to one embodiment of the present disclosure.

Figure 2:
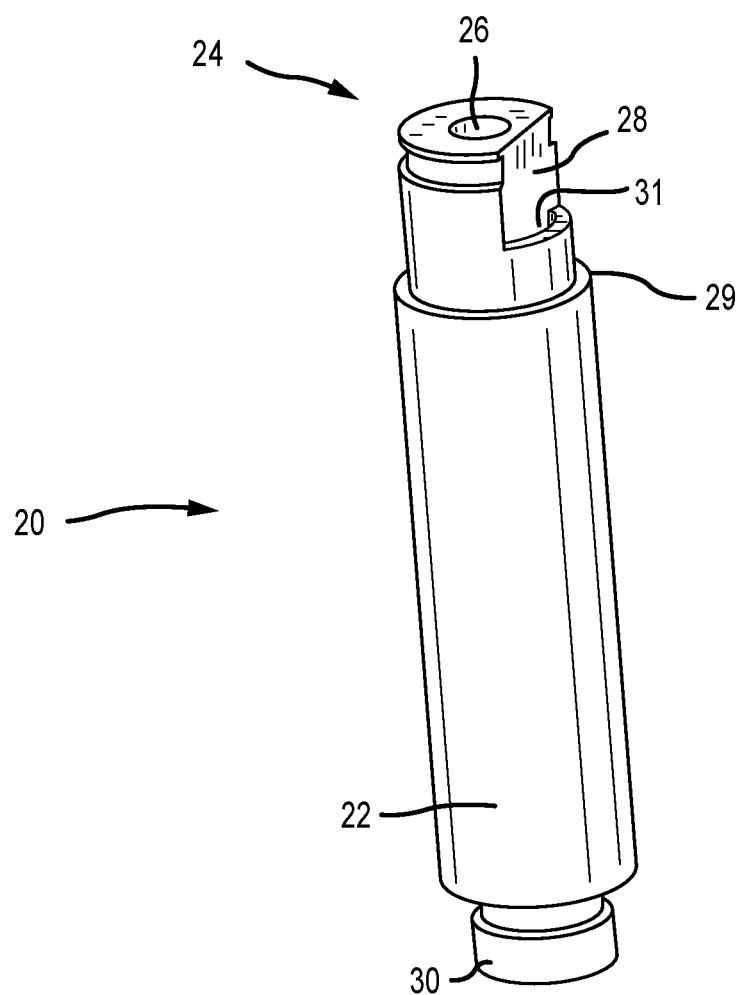

FIG. 2 is a perspective view of a cartridge for use with mouthpieces as contemplated by the present disclosure.

Figure 3:
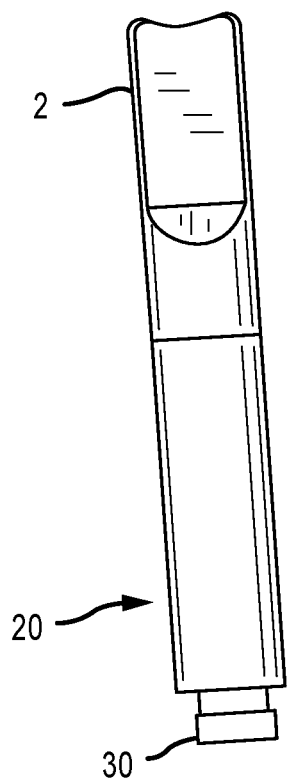

FIG. 3 is a perspective view of a mouthpiece and a cartridge in an assembled state.

Figure 4:
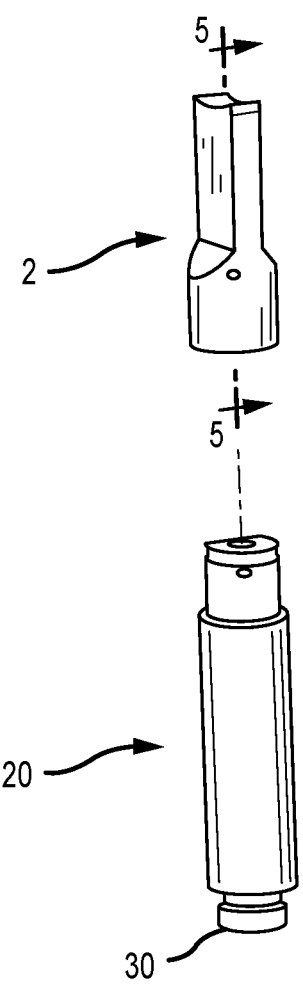

FIG. 4 is an exploded perspective view of the mouthpiece and cartridge according to the embodiment of FIG. 3.

Figure 5:
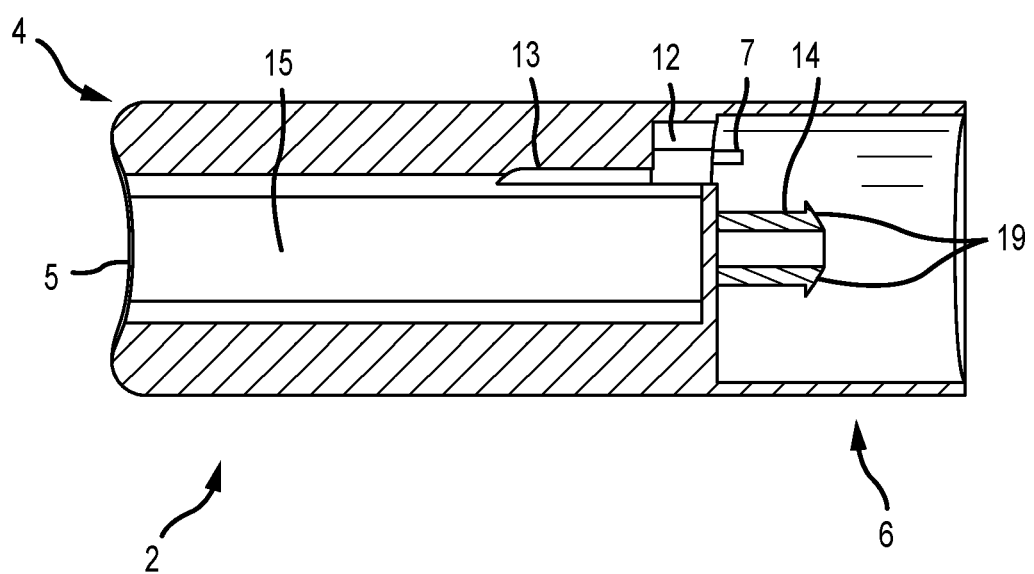

FIG. 5 is a cross-sectional elevation view of a mouthpiece according to one embodiment of the present disclosure.

Figure 6:
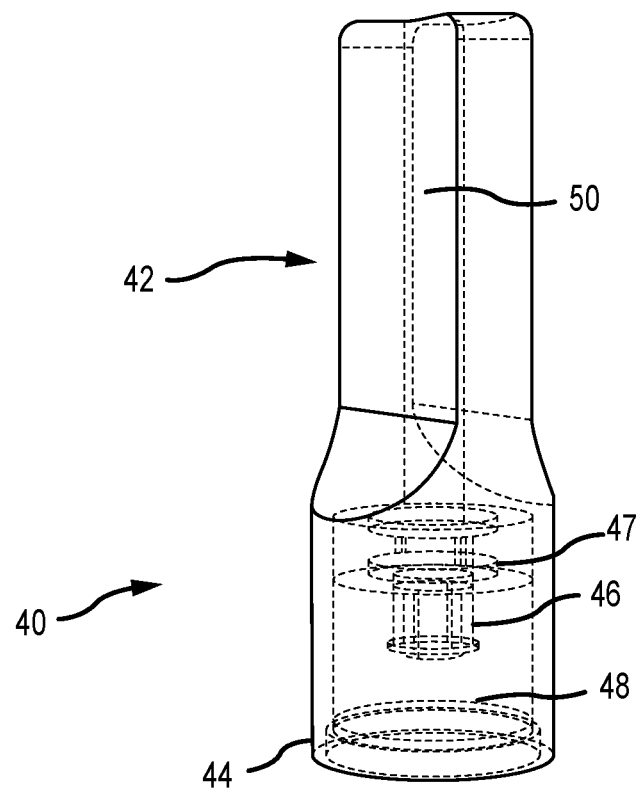

FIG. 6 is a perspective view of a mouthpiece according to one embodiment of the present disclosure, with certain features of a mouthpiece shown in phantom.

Figure 7:
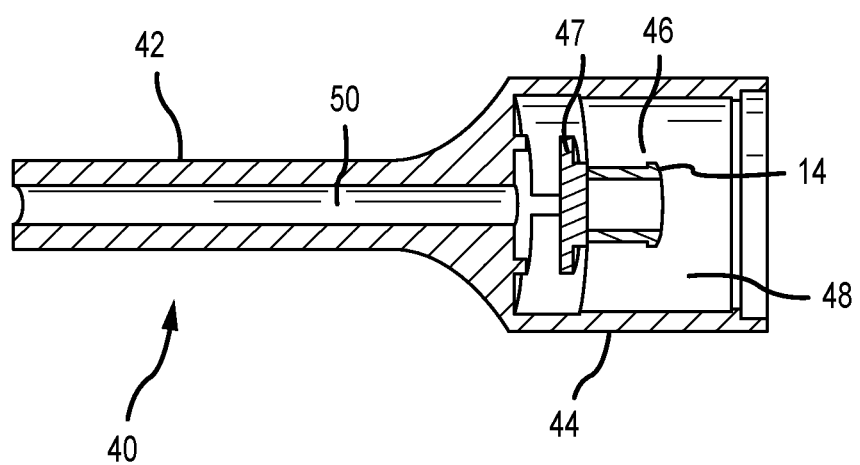

FIG. 7 is a cross-sectional elevation view of the mouthpiece according to the embodiment of FIG. 6.

Figure 8:
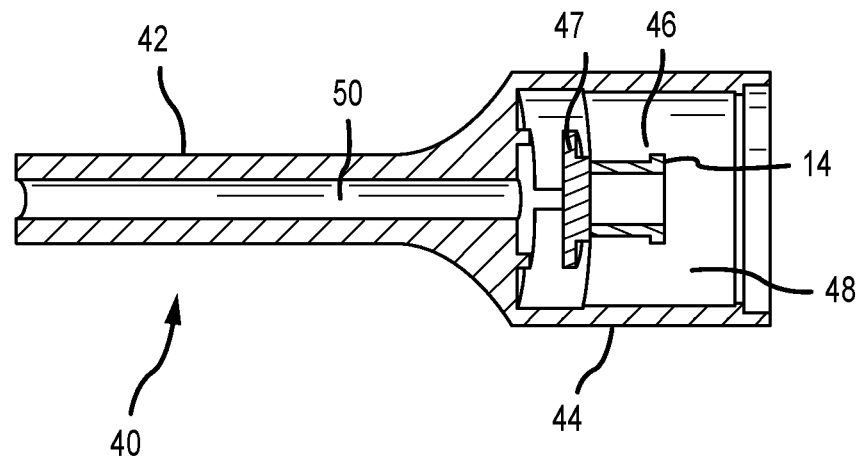

FIG. 8 is a perspective view of a mouthpiece and cartridge according to yet another embodiment of the present disclosure.

Figure 9:
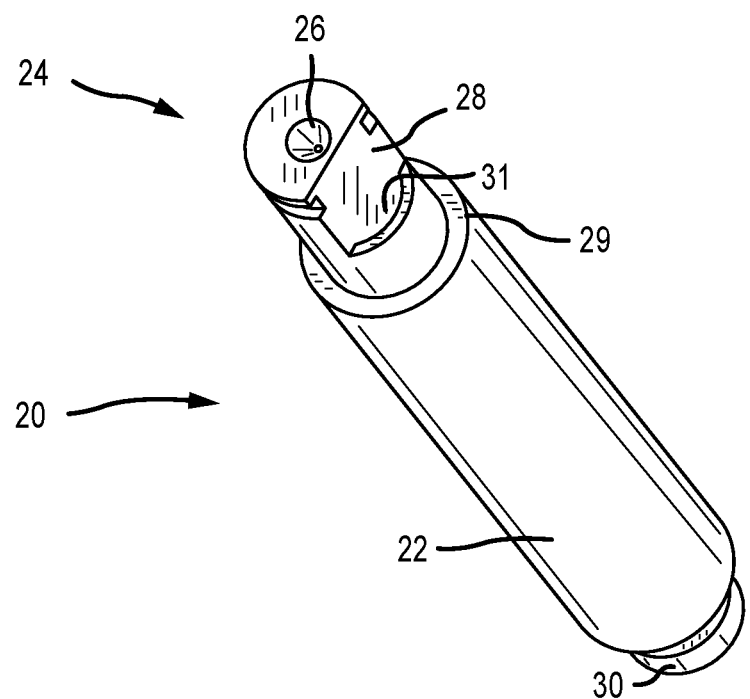

FIG. 9 is a perspective view of a cartridge according to one embodiment of the present disclosure.

DETAILED DESCRIPTION

FIG. 1 is a perspective view of a mouthpiece 2 according to one embodiment of the present disclosure. The mouthpiece 2 comprises a first end 4 and a second end 6. The first end 4 generally comprises a tapered end that is configured to interface with a user's mouth. The second end 6 comprises a rounded end that is operable to be provided in contact with a cartridge (not shown in FIG. 1). The first end 4 and the second end 6 are preferably co-molded or co-formed such that the mouthpiece 2 comprises a single element. Although the second end 6 is depicted as comprising a circular shape, it is contemplated that the second end 6 may comprise various shapes including, but not limited to, rectangular and polygonal shapes, based on the size and shape of a cartridge to which the mouthpiece is intended to be secured.

The second end 6 comprises an open interior portion with a recessed surface 8 surrounded by an annular member 10. The annular member 10 is operable to be provided in contact with or close proximity to a portion of a cartridge. In an assembled state, wherein the mouthpiece 2 is secured to the cartridge, the interior portion is substantially sealed or covered by the cartridge. At least one airport 12 is provided to enable flow of gas or vapor between a cartridge and the first end of the mouthpiece for intake by a user. First and second projections 7a, 7b are provided to enable proper alignment of the mouthpiece 2 with a cartridge.

As shown in FIG. 1, the mouthpiece comprises first and second connecting members 14a, 14b. Although the embodiment of FIG. 1 comprises first and second connecting members, alternative embodiments are contemplated that comprise fewer and greater numbers of connecting members. For example, a single connecting member may be provided. Alternatively, three or more connecting members may be provided. The connecting members 14a, 14b are operable to be inserted in an aperture provided in a cartridge and to connect and secure the mouthpiece 2 to the cartridge. As illustrated, the connecting members 14a, 14b comprise arcuate, spaced-apart members that are intended to and operable to be inserted into a single aperture provided in a cartridge. The connecting members 14a, 14b may alternatively comprise other geometric or non-geometric shapes and need not be arcuate.

In preferred embodiments, the connecting members 14a, 14b are severable from a remainder of the mouthpiece 2. For example, in some embodiments, a frangible score line is provided at the union of each of the connecting members 14a, 14b and the recessed portion 8 of the mouthpiece. If, for example, a user attempts to remove the mouthpiece 2 from a cartridge by bending or other methods, the connecting members 14a, 14b are operable to be severed and detach from the mouthpiece 2. In such a situation, at least one and preferably both connecting members 14a, 14b will be lodged in the aperture of the cartridge and will block attachment of a new or replacement mouthpiece thereby rendering the cartridge effectively inoperable. Such embodiments dissuade or prevent users from tampering with cartridges and/or re-filling cartridges with various substances.

FIG. 2 is a perspective view of a cartridge 20 contemplated for use with mouthpieces of the present disclosure. As shown, the cartridge 20 comprises a main body portion 22 that has an internal volume that is operable to store and house contents for vaporization. A first end 24 of the cartridge 20 comprises an end that is operable to interconnect to a mouthpiece (see 2 of FIG. 1, for example). The first end 24 comprises an aperture 26 that is operable to receive connecting members 14a, 14b of a mouthpiece 2 (see FIG. 1). The aperture 26 serves as a fill-hole for providing contents to the interior of a cartridge prior to final assembly of the cartridge 20 and the mouthpiece 2.

A fluid passage is provided at least in part by the provision of a chamfered portion comprising a planar portion 28. The planar portion 28 comprises a deviation from the otherwise circular outer edge of the upper end of the cartridge 20. An outlet 31 is provided proximal to a lower portion of the planar portion 28 such that vapor or smoke is allowed to travel from an interior volume of the cartridge to the mouthpiece in a direction that is generally parallel to the surface of the planar portion 28.

An annular lip or ledge 29 is provided, which is operable to be provided in contact with an annular member 10 of a mouthpiece 2. The second end of the cartridge 20 comprises a male connector 30 that is operable to connect to a power source (not shown) for powering the heating element in the cartridge.

FIG. 3 is a perspective view of a mouthpiece 2 and a cartridge 20 provided in an assembled state. The assembled device represents a device that is ready for commercial sale and distribution, and wherein an interior volume of the cartridge 20 has been filled with a substance, and the mouthpiece has been securely attached to the cartridge 20.

FIG. 4 is an exploded view of the cartridge 20 and mouthpiece 2 as shown in FIG. 3. As shown in FIG. 4, the mouthpiece 2 and associated cartridge 20 are operable to be provided or secured such that the two devices are coaxial.

FIG. 5 is a cross-sectional elevation view of a mouthpiece 2 according to one embodiment of the present disclosure. As shown, the mouthpiece 2 comprises a first end 4 and a second end 6. The first end 4 comprises at least one flow port 5 for allowing egress of smoke or vapor from the mouthpiece 2. The flow port 5 is in fluid communication with a channel 15 that extends between the first end and the second end 6 of the device. The channel 15 comprises an interior channel that extends to the airport 12. The airport 12 is adapted and intended to align with the planar portion 28 and the outlet 31 of a cartridge (see FIG. 2, for example) such that vapor can travel from within a cartridge (where it is produced) through the airport 12, and through a passageway 13 connecting the cartridge 20, airport 12, and the channel 15. At least one projection 7 is provided to ensure proper alignment between a cartridge 20 and the mouthpiece 2 such that the outlet 31 of the cartridge is properly aligned to allow fluid flow through the mouthpiece.

As further shown in FIG. 5, a connecting member 14 is provided and is operable to extend into a fill port or aperture 26 of a cartridge 20 such that the aperture 26 is at least partially sealed. The connecting member 14 comprises a detachable member and is preferably detached upon removal or attempted removal of the mouthpiece 2 from the cartridge 20.

The connecting member 14 of FIG. 5 comprises an angled or tapered distal end 19. Although a since connecting member 14 is shown in FIG. 5 based on the cross-sectional nature of the drawing, certain embodiments comprise at least two connecting member 14a, 14b (see FIG. 1, for example). The angled surface of the end 19 of the connecting members allow for ease of insertion of the connecting members 14a, 14b into a cartridge and provide a spring-clip feature wherein the connecting members 14a, 14b are compressed toward each other upon insertion into a cartridge. Preferably, the connecting members 14a, 14b comprise a plastic or similar material with an elastic restoring force and wherein the members 14a, 14b are capable of elastically returning to (or proximal to) an original position once insertion is complete. A cartridge may be provided with a lip or flange to receive and secure the distal ends of the connecting members 14a, 14b and provide a resistance against pull-out of the mouthpiece. In various embodiments, including the embodiment illustrated in FIG. 5, the connecting members of a mouthpiece comprise irreversible connecting members. In such embodiments, connecting or securing a mouthpiece to a cartridge is enabled but removal of the mouthpiece is rendered impossible or difficult without damaging or separating the connecting members from the mouthpiece.

FIG. 6 is a cross-sectional elevation view of a mouthpiece according to another embodiment of the present disclosure. As shown, the mouthpiece 40 comprises a first portion 42 and a second portion 44. The first portion 42 comprises a tapered section adapted for use and contact with a user's mouth. The second portion 44 comprises a second end that is operable to attach to a cartridge (not shown). An air passage 50 is provided that extends between the second portion 44 and the first portion 42. The air passage 50 is operable to transmit a smoke or a vapor from a cartridge to a user for inhalation. The second portion 44 comprises an at least partially hollow portion 48 that receives at least a portion of a cartridge. A connecting member 46 is provided within the at least partially hollow portion 48. The connecting portion 46 is operable to contact and connect to a cartridge. The connecting portion 46 is operable to be press-fit or similarly connected to a female portion (see, for example, 26 of FIG. 2) of a cartridge and is severable upon the application of a removable force. Specifically, the connecting portion 46 is operable to detach from the mouthpiece 40. In certain embodiments, a severable score line is provided at or proximal to the connection between the connecting portion 46 and a remainder of the mouthpiece 40. Accordingly, the mouthpiece may be securely connected to a cartridge to provide an assembled state, and disconnection of the mouthpiece 40 and a cartridge severs the connecting portion 46 and renders at least one of the mouthpiece 40 and the cartridge inoperable for further use.

FIG. 7 is a cross-sectional view of the mouthpiece of FIG. 6, wherein the air passage 50 is illustrated as extending between the at least partially hollow portion 48 and a distal end of the mouthpiece 40. The second portion 44 of the mouthpiece 40 is operable to connect to a cartridge, wherein the cartridge houses a substance (e.g. oil) and the cartridge is operable to vaporize the oil and transmit a vaporized substance through the mouthpiece 40 via the air passage 50.

FIG. 8 is a cross-sectional view of a mouthpiece according to another embodiment of the present disclosure. As shown, the air passage 50 is illustrated as extending between the at least partially hollow portion 48 and a distal end of the mouthpiece 40. The second portion 44 of the mouthpiece 40 is operable to connect to a cartridge, wherein the cartridge houses a substance (e.g. oil) and the cartridge is operable to vaporize the oil and transmit a vaporized substance through the mouthpiece 40 via the air passage 50. The device of FIG. 8 comprises first and second projections 14a, 14b (similar to FIG. 1) that do not comprise angled or tapered ends. A single projection 14 is shown in FIG. 8 due the cross-section. As shown, the projection(s) 14 comprise flat end surfaces provided at approximately a perpendicular angule to a longitudinal axis of the device. The projections therefore comprise a "L" shape and are operable to communicate with female receiving portions as shown and described herein including, for example, the device and features of FIG. 9.

FIG. 9 is a perspective view of a cartridge 20 contemplated for use with mouthpieces of the present disclosure. As shown, the cartridge 20 comprises a main body portion 22 that has an internal volume that is operable to store and house contents for vaporization. A first end 24 of the cartridge 20 comprises an end that is operable to interconnect to a mouthpiece. The first end 24 comprises an angled aperture 26 that is operable to receive connecting members 14a, 14b of a mouthpiece 2 (see FIG. 7). The aperture 26 serves as a fill-hole for providing contents to the interior of a cartridge prior to final assembly of the cartridge 20 and the mouthpiece 2. The angled and generally bowl-shaped geometry of the aperture 26 of the embodiment of FIG. 9 allow for various projections to be inserted therein. The projections 14a, 14b of the embodiments provided in FIGS. 7 and 8, for example, are operable for use with the angled aperture 26 which is a frustoconical void feature.

As shown in FIGS. 6-8, the connecting portion 46 of at least some embodiments of the present disclosure comprises a substantially disc-shaped base member 47. The base member 47 comprises a score line at or proximal to its base and such that the base member 47 is severable with a remainder of the connecting portion. The distal ends of the connecting portion and the opposing base member 47 are operable to secure a connecting portion 46 within an inlet to a cartridge (see 26 of FIG. 9, for example). The base member 47 provides a means for preventing the severed portion of the mouthpiece from falling or otherwise moving into an internal storage volume of a cartridge. With the severed portion (e.g. connecting portion 46 and base member 47) secured in the inlet or aperture 26 of the cartridge, both the mouthpiece and the cartridge are rendered inoperable subsequent to a tampering or breakage event. It will be recognized, however, that the exact location of a severable score line is not critical to the invention and various embodiments further contemplate that connecting portions and extensions of the present disclosure are provided in different locations. For example, in some embodiments, it is contemplated that the first and second connecting members 14a, 14b are severable at a base portion thereof.

Various features and embodiments of pressure washing devices are provided herein. It will be recognized, however, that various features are not necessarily specific to certain embodiments and may be provided on any one or more embodiments. The present disclosure and embodiments provided herein are not mutually exclusive and may be combined, substituted, and omitted. The scope of the invention(s) provided herein is thus not limited to any particular embodiment, drawing, or particular arrangement of features.

While various embodiments of the present disclosure have been described in detail, it is apparent that modifications and alterations of those embodiments will occur to those skilled in the art. However, it is to be expressly understood that such modifications and alterations are within the scope and spirit of the present disclosure. Further, the invention(s) described herein are capable of other embodiments and of being practiced or of being carried out in various ways. In addition, it is to be understood that the phraseology and terminology used herein is for the purposes of description and should not be regarded as limiting. The use of "including," "comprising," or "adding" and variations thereof herein are meant to encompass the items listed thereafter and equivalents thereof, as well as, additional items.

What is claimed is:

1. A mouthpiece for a personal vaporizer device comprising:
    a first end operable to contact the mouth of a user;
    a second end operable to connect to a cartridge;
    the second end comprising an open end and a recessed portion provided within the open end;
    a first connecting member and a second connecting member extending from the recessed portion, the connecting members comprising a first end and a second end and a length extending therebetween;
    wherein the first end of each of the first connecting member and the second connecting member is secured to the recessed portion and each connecting member is operable to receive and connect to a cartridge;
    wherein the second end of each of the first connecting member and the second connecting member includes a lip;
    wherein each of the first connecting member and the second connecting member comprises a flexible member and a frangible score line provided proximal to the first end; and
    wherein each of the first connecting member and the second connecting member comprise a severable feature that is operable to be severed and detach from at least one of the first connecting member and the second connecting member upon an application of a removal force upon the mouthpiece.

2. The mouthpiece of claim 1, further comprising an air passage extending through the mouthpiece.

3. The mouthpiece of claim 1, wherein each of the first connecting member and the second connecting member comprises a flexible plastic extension.

4. The mouthpiece of claim 1, wherein the second end of each of the first connecting member and the second connecting member comprises an angled or tapered distal end.

5. The mouthpiece of claim 1, further comprising a cartridge connected to the second end of the mouthpiece.

6. The mouthpiece of claim 1, further comprising a projection to enable proper alignment of the mouthpiece with a cartridge.

7. The mouthpiece of claim 6, wherein the projection comprises an extension of the mouthpiece formed integrally with the mouthpiece.

8. A mouthpiece for a personal vaporizer device comprising:
    a first end operable to contact the mouth of a user;
    a second end operable to communicate with a cartridge;
    the second end comprising a connecting member extending from the second end, wherein the connecting member is operable to connect to a cartridge; and
    wherein the connecting member comprises a flexible member and a frangible score line, wherein the connecting member comprises a severable feature, wherein the second end of the connecting member comprises a lip, and wherein the severable feature is operable to be severed and detach from the connecting member upon an application of a removal force upon the mouthpiece.

9. The mouthpiece of claim 8, further comprising an air passage extending through the mouthpiece.

10. The mouthpiece of claim 8, wherein the connecting member comprises a flexible plastic extension.

11. The mouthpiece of claim 8, wherein a second end of the connecting member comprises an angled or tapered distal end.

12. The mouthpiece of claim 8, further comprising a cartridge connected to the second end of the mouthpiece.

13. The mouthpiece of claim 8, wherein the mouthpiece comprises first and second connecting members.

14. The mouthpiece of claim 8, further comprising a projection to enable proper alignment of the mouthpiece with a cartridge.

15. The mouthpiece of claim 8, wherein the second end comprises an open end and a recessed portion provided within the open end.

16. A mouthpiece for a vaporizer device comprising:
    a first end for contact with a user;
    a second end operable to communicate with a cartridge;
    an airway extending between the first end and the second end;
    the second end comprising a connecting member operable to connect to a cartridge; and
    wherein the connecting member comprises a flexible member with an angled distal end and a frangible score line, the angled distal end comprising a lip; and
    wherein the connecting member comprises a severable feature that is operable to be severed and detach from the connecting member upon an application of a removal force upon the mouthpiece.

17. The mouthpiece of claim 16, further comprising an air passage extending through the mouthpiece.

18. The mouthpiece of claim 16, wherein a second end of the connecting member comprises an angled or tapered distal end.

19. The mouthpiece of claim 16, wherein the second end comprises an open end and a recessed portion, and wherein the connecting member is provided on the recessed portion.

20. The mouthpiece of claim 1, wherein the removal force comprises at least one of a bending and a tensile force.

* * * * *